US012575876B2

(12) United States Patent
Keller et al.

(10) Patent No.: US 12,575,876 B2
(45) Date of Patent: Mar. 17, 2026

(54) DEVICE FOR TISSUE TREATMENT AND METHOD FOR ELECTRODE POSITIONING

(71) Applicant: Erbe Elektromedizin GmbH, Tuebingen (DE)

(72) Inventors: Sandra Keller, Bisingen (DE); Kathrin Hahn, Nuertingen (DE); Bjoern Seitz, Pfullingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 582 days.

(21) Appl. No.: 17/953,652

(22) Filed: Sep. 27, 2022

(65) Prior Publication Data

US 2023/0108832 A1     Apr. 6, 2023

(30) Foreign Application Priority Data

Oct. 1, 2021     (EP) ..................................... 21200514

(51) Int. Cl.
A61B 18/12          (2006.01)
A61B 5/0538         (2021.01)
(Continued)

(52) U.S. Cl.
CPC .......... A61B 18/148 (2013.01); A61B 5/0538 (2013.01); *A61B 2018/00648* (2013.01); (Continued)

(58) Field of Classification Search
CPC .............. A61B 5/0538; A61B 18/1233; A61B 2018/00904; A61B 2018/00666; A61B 2018/00875; A61B 2018/00869

See application file for complete search history.

(56) References Cited

U.S. PATENT DOCUMENTS 11,045,653 B1 *    6/2021  Makharinsky ..... A61N 1/36842
2003/0130711 A1 *  7/2003  Pearson ............. A61B 18/1477
                                                           607/101

(Continued)

FOREIGN PATENT DOCUMENTS

CN          1596085 A      3/2005
CN        105395247 A      3/2016
(Continued)

OTHER PUBLICATIONS

International Search Report for EP21200514.4, mailed Mar. 25, 2022; 19 pages including machine translation.
(Continued)

*Primary Examiner* — Jaymi E Della
(74) *Attorney, Agent, or Firm* — Fitch, Even, Tabin & Flannery LLP

(57)     ABSTRACT

An instrument (14) is suitable for treatment of lung tumors and other tissues and a respective apparatus (15) detects the correct positioning of instrument (14) and its two electrodes (19, 20) in a suitable target tissue by observation of two parameters (G1, G2) and particularly their time-dependent change. If the change (V1, V2) of the two parameters (G1, G2) exceeds defined thresholds (S1, S2) respectively, a contact between the instrument and the tissue to be treated and thus also the positioning of the instrument in a desired position can be derived therefrom. This remarkably increases treatment safety.

18 Claims, 3 Drawing Sheets

(51) Int. Cl.
*A61B 18/14* (2006.01)
*A61B 18/00* (2006.01)

(52) U.S. Cl.
CPC .............. *A61B 2018/00666* (2013.01); *A61B 2018/00702* (2013.01); *A61B 2018/00827* (2013.01); *A61B 2018/00869* (2013.01); *A61B 2018/00875* (2013.01); *A61B 2018/00904* (2013.01); *A61B 18/1206* (2013.01); *A61B 18/1233* (2013.01); *A61B 2018/1467* (2013.01)

(56) References Cited

U.S. PATENT DOCUMENTS

| | | | | |
|---|---|---|---|---|
| 2010/0298823 | A1* | 11/2010 | Cao | A61B 18/1206 606/34 |
| 2011/0152712 | A1* | 6/2011 | Cao | A61B 5/6852 606/33 |
| 2015/0133911 | A1* | 5/2015 | Batchelor | A61B 18/1206 606/34 |
| 2017/0312009 | A1 | 11/2017 | Paul et al. | |
| 2019/0343581 | A1 | 11/2019 | Panescu et al. | |
| 2020/0261720 | A1* | 8/2020 | Danitz | A61N 1/08 |
| 2021/0038280 | A1 | 2/2021 | Pikramenos | |
| 2021/0068895 | A1 | 3/2021 | Panescu et al. | |
| 2021/0153771 | A1 | 5/2021 | Ting et al. | |
| 2023/0414274 | A1* | 12/2023 | Moss | A61B 18/1492 |

FOREIGN PATENT DOCUMENTS

| | | | |
|---|---|---|---|
| CN | 105873534 | A | 8/2016 |
| CN | 109464186 | A | 3/2019 |
| CN | 111479497 | A | 7/2020 |
| DE | 102019209333 | A1 | 12/2020 |
| EP | 2612612 | A1 | 7/2013 |
| JP | 2009-518130 | A | 5/2009 |
| JP | 2016-537088 | A1 | 12/2016 |
| RU | 2 539 010 | C2 | 1/2015 |
| RU | 2 732 696 | C2 | 9/2020 |
| WO | 2009065140 | A1 | 5/2009 |

OTHER PUBLICATIONS

Japan Patent Office; Notice of Reasons for Refusal in corresponding Japanese Patent Application No. 2022-146155, dated Sep. 19, 2025; 7 pages.

Federal Service for Intellectual Property; Office Action in corresponding Russian Patent Application No. 2022125073/14(054539), dated Sep. 24, 2025; 18 pages.

China National Intellectual Property Administration; Office Action in corresponding Chinese Patent Application No. 202211207096.X, dated Dec. 22, 2025; 24 pages.

* cited by examiner

DEVICE FOR TISSUE TREATMENT AND METHOD FOR ELECTRODE POSITIONING

CROSS REFERENCE TO RELATED APPLICATION

This application claims the benefit of European Patent Application No. 21200514.4, filed Oct. 1, 2021, which is incorporated herein by reference in its entirety.

TECHNICAL FIELD

The invention refers to an electrosurgical device for electro-thermal treatment of biological tissue. In addition, the invention refers to a method for positioning of an instrument being part of the device in the biological tissue.

BACKGROUND

In general it is known to detect and to monitor the contact between a treatment electrode and biological tissue by means of electrical measurements. For this purpose WO 2009/065140 A1 as well as US 2017/0312009 A1 disclose an ablation system as well as a method that provides a feedback of formation of a lesion in real time. For this the degree of the electrical coupling between the ablation electrode and the biological tissue is determined. On this basis the volume of the created lesion can be estimated. For determination of the degree of the contact the phase ratio between the applied voltage and the resulting current can be used. For this purpose a phase measurement circuit is provided.

EP 2 612 612 A1 also proposes to detect the phase position between voltage and current at the treatment electrode of an instrument. For this purpose the recognition is used that the phase relations prior to the contact, during contact as well as after treatment are different from one another in a characteristic manner respectively.

DE 10 2019 209 333 A1 discloses a determination of the type of tissue being in contact with an instrument. For this purpose alternating voltages with different frequencies are supplied to the instrument and introduced into the tissue and the resulting currents are monitored. This method is also denoted as impedance spectroscopy.

During specific coagulation of tissue volumes in living human or animal patients it is frequently important to position the respective instrument and particularly its electrodes in the tissue to be treated and particularly to be coagulated, such that a good treatment result is achieved. Thereby the view of the surgeon on the tissue to be treated is typically limited. This applies particularly, if the tissue to be treated is not exposed, but surrounded and embedded into other tissue that has to be treated with care during the treatment.

Therefrom one object of the invention is derived to provide an electrosurgical device that provides support to the treating person during positioning of the instrument in the tissue to be treated. In addition, it is another object of the invention to provide a respective method.

SUMMARY

These objects are solved with the electrosurgical device as well as the method for tumor localization in healthy tissue as disclosed herein.

An instrument having preferably a longitudinal needle or pin-like basic shape that can be penetrated into biological tissue is part of the electrosurgical device according to the invention. Preferably the instrument comprises two or more electrodes that are arranged with axial distance to each other on the instrument. For example, the instrument is a hose-like instrument that can be inserted into a body, e.g. through an endoscope, having a distal end section in which the electrodes are arranged realized as coil electrodes, cylinder electrodes or the like. The instrument can be cooled from the interior in order to block or limit heating of the electrodes. The electrodes preferably arranged in axial distance to one another preferably serve as treatment electrodes and can be supplied with a treatment voltage $U_{HF}$ for this purpose. They are connected with an electrosurgical generator for this purpose that is configured to output such a treatment voltage $U_{HF}$. The treatment voltage $U_{HF}$ is a radio frequency alternating voltage having a frequency of typically higher than 100 kHz. In addition, the generator is configured to output a test voltage $U_T$ to the same electrodes that is remarkably less than the treatment voltage $U_{HF}$ (e.g. factor of 10-20 fold) and has therefore no or only a very modest physiological effect. The test voltage $U_T$ serves for checking and displaying the positioning of the instrument in the biological tissue, e.g. in a target tissue, such as a tumor, that shall be subject to the treatment voltage $U_{HF}$ and thermally destroyed thereby in the following after correct positioning of the instrument.

The invention uses the characteristic that tumorous tissue is very well supplied with blood and therefore electrically distinguishes from adjoining healthy tissue. The instrument being part of the device can be reliably positioned in the tumor tissue based on this characteristic of the tumor. Misplacements are avoided.

The generator comprises a control device that is configured to detect the current i created by the test voltage $U_T$ between the two electrodes of the instrument. In addition, the control device is configured to determine two characteristic parameters from the test voltage $U_T$ and the current i. One of the two parameters depends on the impedance effective between the electrodes. The other of the two parameters depends on the phase angle between the test voltage and the current. For example, the first parameter can be the amount of the impedance, while the second parameter is the power factor or another parameter depending on the phase angle phi between the current and the voltage. Power factor means the quotient of the real power effective and converted between the electrodes in the tissue relative to the apparent power.

The control device monitors the change of the two parameters during penetration of the instrument into the biological tissue and checks whether the two changes are exceeding respectively predefined thresholds. The changes of the two parameters can be understood as time-dependent change. The change of the respective parameter is then measured as difference of the parameter occurring between two subsequent points in time of a defined time interval.

The control device can be configured in different manners:

In a first variant it can be configured to always output a signal, if the changes of the two parameters exceed their two thresholds.

In another variant the control device can be configured to output a first signal, if the changes exceed their two thresholds in a first direction and output a second signal, if the changes turn their directions subsequently.

In another variant the control device can be configured to set the two parameters as reference parameters, if both changes exceed predefined thresholds respectively. The definition of the two reference parameters can be correlated with the output of a first signal as an option that indicates to the surgeon that the target tissue has been reached. In addition, the control device can be configured to output a second signal, if a difference results between the two parameters and the reference parameters that exceeds a predefined amount. Alternatively, the control device can be configured to output the second signal, if the changes change their directions after setting the reference parameters. The first signal and the second signal can be equal or different. It is also possible to create a signal as long as the two parameters do not deviate from the two reference parameters (within a defined or a definable tolerance range).

The signal that is output can be, for example, an acoustic signal, an optical signal or a combination of both, wherein the optical signal can be displayed visually on a display of an electrosurgical system comprising the electrosurgical generator.

According to the concept of the invention, the treating person penetrates the instrument with usual speed into the tissue. Usual penetration speeds are approximately around 0.5 cm/s. For the example of the treatment of lung tumors an impedance Imp of more than 300 Ohm and a power factor of LF=cos(phi)<0.75 results in healthy lung tissue. As soon as one of the electrodes, particularly the distal electrode of the instrument, gets in contact with tumor tissue, both parameters change, i.e. the impedance as well as the power factor, for example. If the instrument is now further penetrated into the target tissue and the distal end of a proximal electrode gets in contact with the target tissue, the impedance drops in case of usual penetration speed and usual instrument size within a time period, e.g. 2 seconds, about at least 60% relative to the impedance measured before, while the power factor increases, e.g. about 20%, relative to the power factor prior to the defined time period (e.g. 2 seconds). This particularly applies for usual instruments having an electrode length of 8 to 9 mm in axial direction and an axial electrode distance of 3 to 4 mm. The changes of the two parameters are detected by the control device. It can output a signal accordingly from which the treating person can conclude that both electrodes are in contact with the tumor tissue. According to the alternative embodiments of the control device mentioned above, it can also store the values of the parameters as reference parameters instead of the direct signal output or in addition to this, if the parameters change relative to the stored reference parameters. For example, the position of the electrodes on the instrument inside the target tissue can be indicated to the user on a display provided on the apparatus 15.

During measurement of the two parameters, i.e. the impedance and the power factor, for example, preferably multiple subsequent values are measured respectively and a floating average is determined therefrom. For example, the first parameter can be the floating average of the impedance, while the second parameter is the floating average of the power factor. The device according to the invention can be configured to compare and set the floating averages at different points in time with one another, wherein the points in time relate to each other in a defined time interval. In doing so, the treating person can carry out an adjustment of its individual penetration speed. If he inserts the electrodes rather slowly, he should select a larger time interval, if he tends to insert the instrument rather fast, he should tend to select a shorter time interval.

In addition, it is possible to carry out the penetration process automatically, in that a drive device is provided that moves the instrument in distal direction with known, e.g.

constant speed and/or in a displacement controlled manner. Thereby the drive device can create position data that characterize the respective position of the instrument relative to its longitudinal direction. In this case the changes can be determined as time-dependent changes or alternatively as position-dependent changes. The latter is also possible during manual penetration of an instrument, if it is in connection with a suitable displacement measurement device. Such a displacement measurement device can provide data, for example, that indicate how far the instrument has been moved in distal axial direction. In the simplest case, such a displacement measurement device can be provided on an endoscope or bronchoscope, in which, for example, a measurement wheel is provided at its proximal end that is in contact with the instrument body (of the probe) and is rotated, if the probe is axially forwarded.

BRIEF DESCRIPTION OF THE DRAWINGS

Additional advantageous details of the invention are subject of dependent claims as well as the description and the assigned drawings. The drawings show:

DETAILED DESCRIPTION

Figure 1:
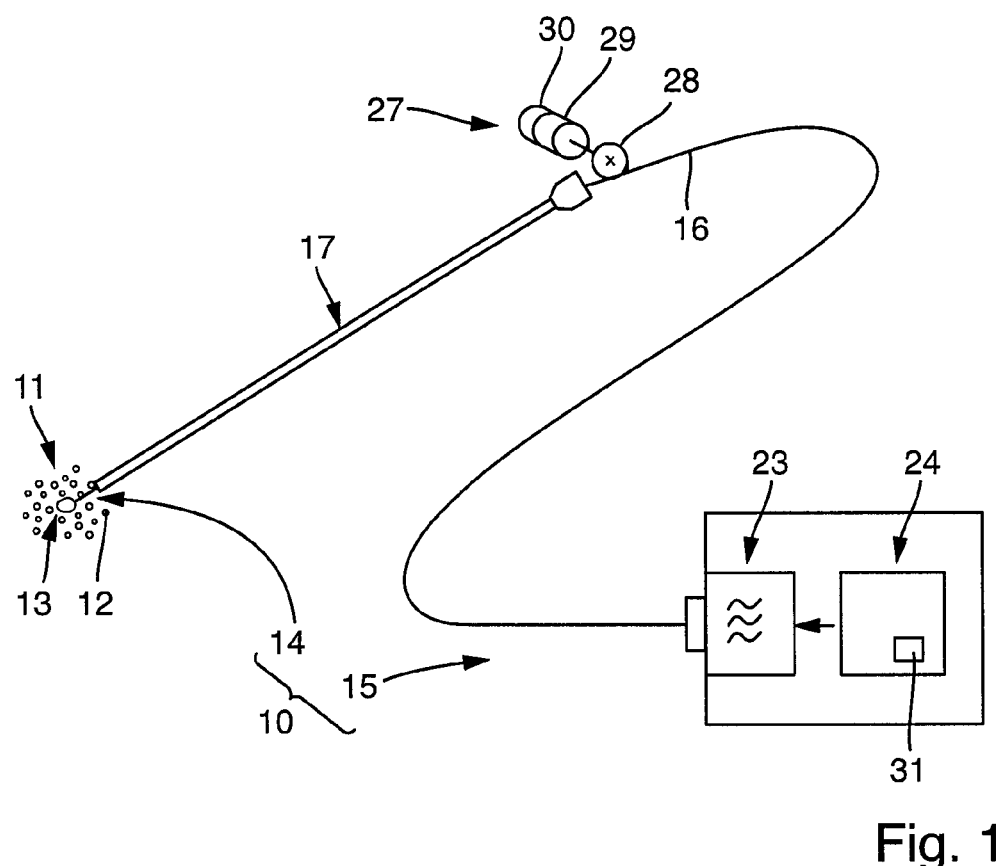
FIG. 1 the device according to the invention during treatment of biological tissue in a schematic illustration, FIG. 2 the instrument being part of the device according to FIG. 1 during penetration in tissue that needs to be treated, FIG. 3 the instrument according to FIG. 2 in a schematic longitudinally cut illustration in part, FIG. 4 voltage and current at the instrument during penetration and during treatment, FIG. 5 different parameters determined from the voltage and the current in a time-dependent progress as diagram.

A device 10 is illustrated in FIG. 1 that serves for treatment of biological tissue 11, such as lung tissue, that consists of healthy lung tissue 12 and a tumor 13 embedded therein, for example. The device 10 comprises at least an instrument 14 and an apparatus 15 for supply of the instrument 14 with the necessary operating media, e.g. cooling media and current. The instrument 14 can be a flexible probe 16 that can be guided to the target tissue 11, e.g. through a bronchoscope 17.

During the treatment of other tissue, also other instruments, e.g. an endoscope, instruments for laparoscopic use or also open surgical instruments can be used. The invention is not limited to bronchoscopy.

Figure 2:
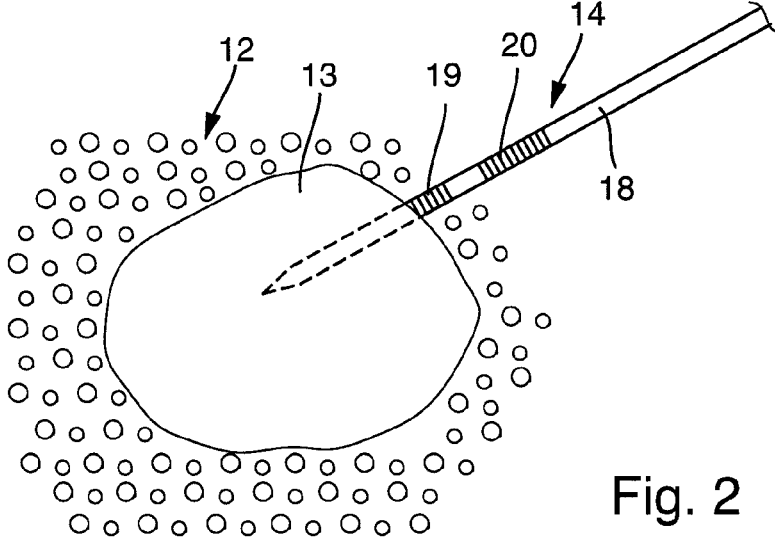
Figures 3, 4:
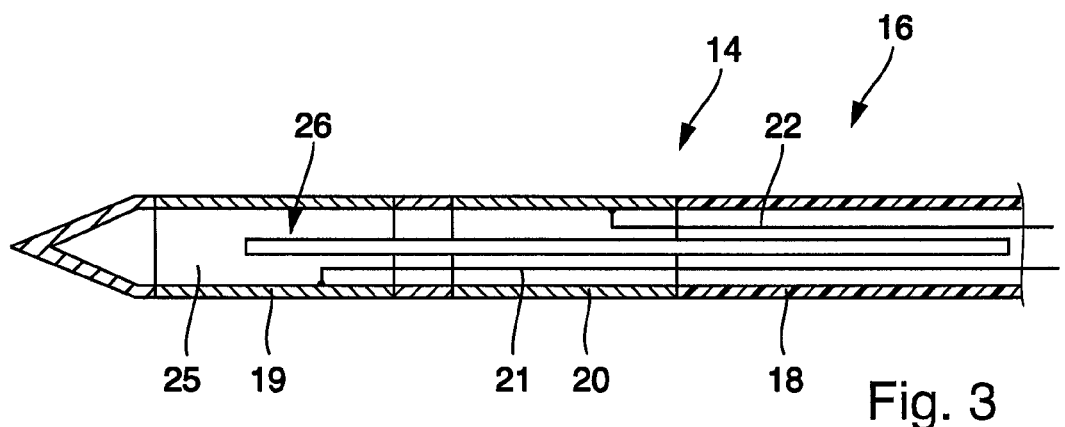

The instrument 14 is further illustrated in FIGS. 2 and 3. It comprises a longitudinal body 18, e.g. configured as hose, on which a distal electrode 19 and with distance in proximal direction a second electrode 20 are arranged. The electrodes 19, 20 typically have a length in axial direction between 7 and 10 mm and are electrically insulated with regard to each other. For this purpose they are arranged in a distance of 3 mm to 5 mm in axial direction, for example. The electrodes 19, 20 are realized as cylindrical sleeves, coils or the like, for example, and have a diameter of 2 to 3 mm, for example.

The electrodes 19, 20 can be supplied with voltage and current via electrical lines that preferably extend through the probe 16 and are connected to the apparatus 15. In FIG. 1 the apparatus 15 comprises an RF generator 23 for this purpose that is controlled by means of a control device 24 in order to either provide a test voltage $U_T$ or a treatment voltage $U_{HF}$ to the electrodes 19, 20.

The instrument 14 can surround a lumen 25 to which cooling medium is supplied via a capillary 26 arranged inside lumen 25. This cooling medium can serve to cool the electrodes 19, 20 in order to avoid dry out of the tissue being in contact with the electrodes 19, 20 during treatment.

As illustrated in FIG. 1, as an option a displacement measurement device 27 can be provided on the bronchoscope 17 by means of which the present position of the probe 16 during insertion in the bronchoscope 17 and during penetration into the biological tissue 11 can be determined. A wheel 28 being in frictional contact with the probe 16 and a resolver 29 can be part of the displacement measurement device, for example. Alternatively, displacement markings can be attached to the coating of probe 16 that can be read by the displacement measurement device 27. It is in addition possible to penetrate probe 16 in an automated manner into the tissue 11. For this purpose a motor 30 can be provided that is drivingly coupled with wheel 28. The resolver 29 or the other displacement measurement device 27 and, if provided, motor 30 are then connected with control device 24.

The control device 24 can comprise an input means 31, such as a keyboard, a touchscreen or the like, in order to be able to influence its operation. The input means can be configured to input predefined values, e.g. for time periods, voltages, currents, powers, thresholds and the like and to transmit them to the control device.

The generator 23 is configured to output a treatment voltage $U_{HF}$ and alternatively a test voltage $U_T$ illustrated in FIG. 4 in the diagram that can have an amount of a few Volts, e.g. only 10 Volts. The test voltage $U_T$ is preferably an alternating voltage, particularly a radio frequency alternating voltage having a frequency over 100 kHz. It is transmitted to the electrodes 19, 20 via lines 21, 22.

During penetration into the tissue 11 a current i flows between the electrodes 19, 20. Generator 23 comprises respective measurement means in order to detect the current i in its magnitude, but also with regard to its phase position in relation to the test voltage $U_T$. The measurement means can detect, as an example, the phase angle phi between the test voltage $U_T$ and the resulting current i or a parameter depending from the phase angle phi (e.g. the power factor).

The generator 23 is in addition configured to output the treatment voltage $U_{HF}$ that can have an amount of 100 Volts or multiple 100 Volts, for example (however preferably <200 Vp). In addition, generator 23 can be configured to detect thereby the resulting current. However, this is not mandatory.

The control device 24 is configured to supply the electrodes 19, 20 during penetration of the instrument 14 into the tissue 11 with a test voltage via generator 23. Thereby control device 24 is in addition configured to determine a first parameter G1 from the voltage $U_T$ and the current i that depends on the impedance Imp effective between electrodes 19, 20. This parameter G1 can be, for example, the complex impedance Imp, the real part R=Re{Imp} thereof, the amount |Imp| thereof or another parameter derived therefrom, e.g. the conductance $Imp^{-1}$. The first parameter G1 can also be represented by other parameters derived from the impedance Imp.

In addition, control device 24 is configured to determine a second parameter G2 that depends, for example, from the phase angle phi between current i and test voltage $U_T$. The second parameter G2 can be, for example, the power factor LF=cos(phi). The power factor LF can also result from the quotient of the effective power P transferred into the tissue 11 and the apparent power S, LF=P/S.

In addition, control device 24 is configured to determine the change V1 of first parameter G1 and the change V2 of second parameter G2. As an example, the change can be the time-dependent change. For this purpose a floating average can be created from the first parameter G1 and the difference of this average between two points in time can be determined. The two points in time t1, t2 can have a distance of a non-varying defined time interval Δt. The time interval Δt can be a time interval that can be input by means of the input device 31, for example. It can be, for example, between 0.1 and 5 seconds and can be adjusted to two seconds, for example. In doing so, the first change V1 is the difference between the first parameter G1 at a point in time t2 and a point in time t1 that have a distance from one another about the time interval Δt.

Figure 5:
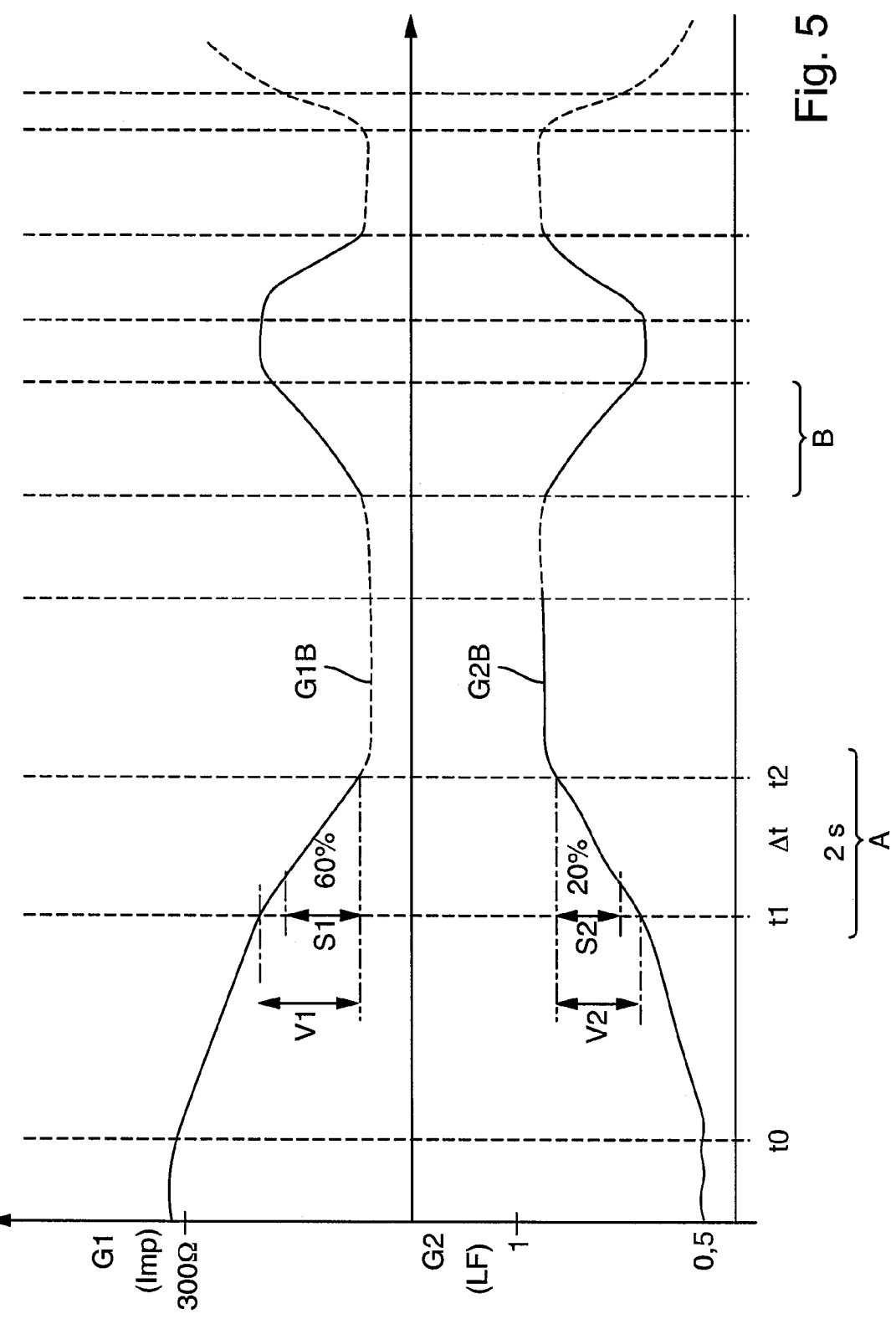

These circumstances are illustrated in FIG. 5. Also the second change V2 can be understood as difference of the second parameter G2 between two different points in time t1, t2. This difference is in turn preferably determined between average values of the second parameter G2. For example, the second parameter G2 is the floating average of the power factor. In this example the difference is determined from the floating average of the power factor LF at the point in time t2 and the floating average of the power factor LF at the point in time t1.

The control device 24 is configured to determine the two changes V1 and V2 during penetration of the instrument 14 into the tissue 11. This is illustrated in FIG. 5. First, the two electrodes 19, 20 are located in lung tissue 12 on the very left in FIG. 5. The impedance or its amount and thus the parameter G1 are on a comparably high value above 300 Ohms. The power factor LF is in a range of cosine phi<0.75.

At a point in time t0 electrode 19 gets in contact with tumor 13. During continued penetration of instrument 14 into the tumor 13 the impedance starts to decrease gradually. Concurrently the power factor LF increases gradually. As soon as the second electrode 20 also penetrates into tumor 13 (point in time t1), the impedance Imp starts to decrease quicker and the power factor LF starts to increase quicker. This is apparent in FIG. 5 in section A by the steeper decrease of curve of G1 and the steeper increase of curve of G2 in the time window Δt (it is indicated that the progress of the parameters G1 and G2 in FIG. 5 is illustrated based on the floating average respectively, i.e. a sequence of measurement values, e.g. within a passed interval of 1 second, is processed to obtain an average value for determination of the parameter G1 and the parameter G2 respectively).

If the amount of the difference of the floating averages of G1 in the interval A, i.e. a change V1, exceeds 60% and the change V2 (i.e. the amount of the difference of the floating average of G2 in the interval A) exceeds 20%, the control device 24 can carry out different actions, depending on the configuration. A first option is the immediate output of a signal that indicates the operator that both electrodes 19, 20 are sufficiently located inside tumor 13. In doing so, the treatment of tumor is released. A second option is the output of the signal after a non-varying or adjustable waiting period. This considers the circumstance that the changes V1 and V2 already fulfill the above requirements in most cases before the proximal electrode is completely penetrated into the tumor. The waiting period, e.g. 1 second, results in that the user moves the probe somewhat deeper into the tumor. The treating person can now switch the generator from the test mode into the treatment mode and can thus apply the treatment voltage to the electrodes 19, 20. This can be carried out manually as well as automatically by means of the control device 24 in a modified embodiment.

In another variant the control device 24 can also store the parameters G1 and G2 at the end of phase A as reference parameters G1B, G2B and can output a signal only if both parameters G1, G2 start to change in an opposite sense, as illustrated in FIG. 5 in section B.

The device 10 described so far operates as follows:

After connection of instrument 14 to the apparatus 15, instrument 14 is guided to the tissue 11 to be treated through the bronchoscope 17. The instrument 14 is then moved out of the bronchoscope 17 in distal direction and is penetrated into the tissue 11. As soon as the electrodes 19, 20 of instrument 14 are no longer visible by the user, the treating person activates generator 23 in the test mode, such that it outputs the test voltage $U_T$ to the electrodes 19, 20 of instrument 14. Thereby generator 23 applies a low sinusoidal alternating voltage of, for example, less than 10 $V_p$ (Volt peak) having a frequency of, e.g. 350 kHz with power limitation of 1 Watt to the instrument 14. The test voltage $U_T$ and the current i resulting therefrom have no thermal effect on the tissue 11 due to their low power.

In the test mode instrument 14 is forwarded further inside tissue 11, whereby the impedance Imp and the phase angle phi or parameters G1, G2 derived therefrom, such as the power factor LF, are determined and stored in defined time intervals (e.g. in a distance of 0.1 milliseconds). As long as the instrument 14 is located in the lung tissue 12, the impedance Imp is in the range of above 300 Ohm and the power factor LF is typically less than 0.75.

As soon as the distal electrode 19 of instrument 14 gets in contact with tumor tissue 13, the impedance Imp as well as the power factor LF start to change in a characteristic manner. Thereby the ablation instrument 14 is further penetrated into the tumor tissue 13.

If the change V1 of the present value of the impedance Imp compared to an impedance Imp prior to a defined time interval (e.g. Δt=2 seconds) exceeds a threshold S1 (e.g. 60%) and concurrently the change V2 of the present power factor LF compared with the power factor LF 2 seconds ago exceeds a threshold S2 (e.g. 20%), these momentary values of the impedance Imp and the power factor LF are defined as tumor values. The control device can be configured to store the present values G1 and G2 as reference values G1B and G2B.

Instead of a time interval Δt of two seconds depending on the treating person, also other time intervals can be adjusted and used. A change of this time interval Δt can be carried out by means of the input device 31.

The user now moves the instrument 14 further through the tumor 13. As soon as the control device 24 detects an increase of the currently calculated average of the calculated floating average of the impedance value and a decrease of the floating average of the power factor (FIG. 5, section B), the control device indicates a signal to the user that indicates that the instrument is now again in contact with lung tissue. This means that the instrument 14 with its electrodes 19, 20 is located non-symmetrically inside tumor 13 or has completely penetrated through tumor 13. The user recognizes this situation based on the signal which is, for example, displayed on a display arranged on the apparatus 15 and can retract the ablation instrument. In this way the user finds a position that is suitable for treatment. The signal output can be carried out in section B, if the changes V1, V2 exceed a respective threshold. The thresholds can be identical to the thresholds S1 and S2 or can be different therefrom.

In a modified embodiment control device outputs in section A (FIG. 5) a first signal and in section B a second signal, such that the user finds the correct position of the instrument 14 between the sections A and B.

An instrument 14 is suitable for treatment of lung tumors and other tissues and a respective apparatus 15 detect the correct positioning of instrument 14 and its two electrodes 19, 20 in a suitable target tissue by observation of two parameters G1, G2 and particularly their time-dependent change. If the change V1, V2 of the two parameters G1, G2 exceeds defined thresholds S1, S2 respectively, a contact between the instrument and the tissue to be treated and thus also the positioning of the instrument in a desired position can be derived therefrom. The invention thus remarkably contributes for increasing treatment safety.

LIST OF REFERENCE SIGNS 10 device
11 biological tissue
12 healthy lung tissue
13 tumor
14 instrument
15 apparatus
16 probe
17 bronchoscope
18 base body
19 first electrode
20 second electrode
21, 22 lines
23 generator
24 control device
25 lumen
26 capillary
27 displacement measurement device
28 wheel
29 resolver
30 motor
31 input means

The invention claimed is:

1. An electrosurgical device for electro-thermal treatment of biological tissue, the electrosurgical device comprising:

an instrument configured to penetrate the biological tissue and including a body having a first electrode and at least one second electrode arranged proximally to the first electrode which are configured to be supplied with a radio frequency test voltage and with a radio frequency treatment voltage;

an apparatus that comprises an electrosurgical generator that is configured to supply the first and at least one second electrodes of the instrument with the radio frequency test voltage and to detect a resulting current thereby; and a control device that is configured to determine from the radio frequency test voltage and the current a first parameter that depends on an effective impedance between the first and at least one second electrodes and a second parameter that depends on a phase angle between the radio frequency test voltage and the current;

wherein the control device is further configured to determine whether:

a first change of the first parameter exceeds a first threshold, and a second change of the second parameter exceeds a second threshold;

wherein the first parameter is an impedance, and the second parameter is a power factor;

wherein the first threshold is a decrease of 60%.

2. The electrosurgical device according to claim 1, wherein the first change and the second change are changes of the first and second parameters, respectively, measured at different points in time.

3. The electrosurgical device according to claim 1, wherein the control device is configured to determine the first and second parameters as averages, respectively, from multiple subsequent determinations of the first and second parameters.

4. The electrosurgical device according to claim 2, wherein the control device is connected with an input means configured to adjust a time interval defined by the different points in time.

5. The electrosurgical device according to claim 1, wherein the control device is configured to define a value of the first parameter as a first reference parameter and a value of the second parameter as a second reference parameter, if both the first and second changes have exceeded the first and second thresholds in respective first directions.

6. The electrosurgical device according to claim 5, wherein the control device is configured to output a signal if the first and second parameters change in respective second directions starting from the first and second reference parameters that are opposite to the respective first directions.

7. The electrosurgical device according to claim 1, wherein a displacement measurement device is assigned to the instrument and the control device is configured to detect the first and second changes in a displacement dependent manner, wherein the control device is configured to determine the first and second changes by differences between subsequent determinations of the first and second parameters determined at different instrument positions.

8. The electrosurgical device according to claim 1, wherein the second change is an increase of the power factor exceeding the second threshold.

9. The electrosurgical device according to claim 8, wherein the second threshold is 20%.

10. A method for tumor localization in the biological tissue using an instrument according to claim 1, the method comprising:
  penetrating the instrument into the biological tissue;
  supplying the radio frequency test voltage to the first and the at least one second electrodes and detecting the resulting current;
  determining from the test voltage and the current the first parameter depending on the effective impedance between the first and the at least one second electrodes and the second parameter depending on the phase angle between the test voltage and the current; and
  determining whether:
    the first change of the first parameter exceeds the first threshold, and
    the second change of the second parameter exceeds the second threshold.

11. An electrosurgical device for electro-thermal treatment of biological tissue, the electrosurgical device comprising:
  an instrument configured to penetrate the biological tissue and including a body having a first electrode and at least one second electrode arranged proximally to the first electrode which are configured to be supplied with a radio frequency test voltage and with a radio frequency treatment voltage;
  an apparatus that comprises an electrosurgical generator that is configured to supply the first and at least one second electrodes of the instrument with the radio frequency test voltage and to detect a resulting current thereby; and
  a control device that is configured to determine from the radio frequency test voltage and the current a first parameter that depends on an effective impedance between the first and at least one second electrodes and a second parameter that depends on a phase angle between the radio frequency test voltage and the current;
  wherein the control device is further configured to determine whether:
    a first change of the first parameter exceeds a first threshold, and
    a second change of the second parameter exceeds a second threshold;
  wherein the first parameter is an impedance and the second parameter is a power factor;
  wherein the second threshold is an increase of 20%.

12. The electrosurgical device according to claim 11, wherein the first change and the second change are changes of the first and second parameters, respectively, measured at different points in time.

13. The electrosurgical device according to claim 11, wherein the control device is configured to determine the first and second parameters as averages, respectively, from multiple subsequent determinations of the first and second parameters.

14. The electrosurgical device according to claim 12, wherein the control device is connected with an input means configured to adjust a time interval defined by the different points in time.

15. The electrosurgical device according to claim 11, wherein the control device is configured to define a value of the first parameter as a first reference parameter and a value of the second parameter as a second reference parameter if both the first and second changes have exceeded the first and second thresholds in respective first directions.

16. The electrosurgical device according to claim 15, wherein the control device is configured to output a signal if the first and second parameters change in respective second directions starting from the first and second reference parameters that are opposite to the respective first directions.

17. The electrosurgical device according to claim 11, wherein a displacement measurement device is assigned to the instrument and the control device is configured to detect the first and second changes in a displacement dependent manner, wherein the control device is configured to determine the first and second changes by differences between subsequent determinations of the first and second parameters determined at different instrument positions during penetration of the instrument into the biological tissue.

18. The electrosurgical device according to claim 11, wherein the first threshold is a decrease of 60%.

* * * * *